(12) United States Patent
Sato et al.

(10) Patent No.: US 11,687,049 B2
(45) Date of Patent: Jun. 27, 2023

(54) INFORMATION PROCESSING APPARATUS AND NON-TRANSITORY COMPUTER READABLE MEDIUM STORING PROGRAM

(71) Applicant: Agama-X Co., Ltd., Tokyo (JP)

(72) Inventors: Masahiro Sato, Kanagawa (JP); Kengo Tokuchi, Kanagawa (JP)

(73) Assignee: Agama-X Co., Ltd., Tokyo (JP)

( * ) Notice: Subject to any disclaimer, the term of this patent is extended or adjusted under 35 U.S.C. 154(b) by 557 days.

(21) Appl. No.: 16/746,982

(22) Filed: Jan. 20, 2020

(65) Prior Publication Data

US 2021/0063978 A1    Mar. 4, 2021

(30) Foreign Application Priority Data

Aug. 26, 2019   (JP) ................. 2019-153629

(51) Int. Cl.
*G10L 15/22*   (2006.01)
*A61B 5/378*   (2021.01)
*A61B 5/381*   (2021.01)
*G05B 15/02*   (2006.01)

(52) U.S. Cl.
CPC .............. *G05B 15/02* (2013.01); *A61B 5/378* (2021.01); *A61B 5/381* (2021.01); *G10L 15/22* (2013.01); *G10L 2015/223* (2013.01)

(58) Field of Classification Search
None
See application file for complete search history.

(56) References Cited

U.S. PATENT DOCUMENTS

| | | | |
|---|---|---|---|
| 2010/0010365 A1 | 1/2010 | Terao et al. | |
| 2012/0245713 A1* | 9/2012 | Chen | G06F 3/01 700/83 |
| 2013/0053720 A1* | 2/2013 | Sakaguchi | A61B 5/377 600/544 |
| 2014/0277582 A1* | 9/2014 | Leuthardt | A61B 5/0006 623/25 |
| 2020/0201442 A1 | 6/2020 | Chikuri | |

FOREIGN PATENT DOCUMENTS

| | | |
|---|---|---|
| JP | 2010-019708 | 1/2010 |
| JP | 2015211705 | 11/2015 |
| JP | 2016067922 | 5/2016 |
| JP | 6067808 | 1/2017 |
| JP | 6340528 | 6/2018 |
| WO | WO 2018/235191 | 12/2018 |

* cited by examiner

*Primary Examiner* — Isaac Tuku Tecklu (57) ABSTRACT

An information processing apparatus includes a processor configured to associate information indicating a recognition result of a voice of a user uttered at a time at which the user manually operates a device, biological information other than the voice of the user, and manual operation information indicating a manual operation for the device with each other, and operate the device based on the biological information in a subsequent operation.

18 Claims, 3 Drawing Sheets

| ID | DEVICE INFORMATION | MANUAL OPERATION INFORMATION | VOICE INFORMATION | BRAIN WAVES | CONTROL INFORMATION |
|---|---|---|---|---|---|
| 1 | AIR CONDITIONER α | PRESS POWER BUTTON AT THE TIME OF POWER IS TURNED OFF | SWITCH ON |  | POWER ON |
| 2 | AIR CONDITIONER α | PRESS POWER BUTTON AT THE TIME OF POWER IS TURNED ON | SWITCH OFF |  | POWER OFF |
| ... | ... | ... | ... | ... | ... |

FIG. 4

| ID | DEVICE INFORMATION | MANUAL OPERATION INFORMATION | VOICE INFORMATION | BRAIN WAVES | USER INFORMATION | CONTROL INFORMATION |
|---|---|---|---|---|---|---|
| 1 | AIR CONDITIONER α | PRESS POWER BUTTON AT THE TIME OF POWER IS TURNED OFF | SWITCH ON | ～ | USER A | POWER ON |
| 2 | AIR CONDITIONER α | PRESS POWER BUTTON AT THE TIME OF POWER IS TURNED OFF | SWITCH ON | ～ | USER B | POWER ON |
| 3 | AIR CONDITIONER α | PRESS POWER BUTTON AT THE TIME OF POWER IS TURNED ON | SWITCH OFF | ～ | USER A | POWER OFF |
| ... | ... | ... | ... | ... | ... | ... |

INFORMATION PROCESSING APPARATUS AND NON-TRANSITORY COMPUTER READABLE MEDIUM STORING PROGRAM

CROSS-REFERENCE TO RELATED APPLICATIONS

This application is based on and claims priority under 35 USC 119 from Japanese Patent Application No. 2019-153629 filed Aug. 26, 2019.

BACKGROUND

(i) Technical Field

The present invention relates to an information processing apparatus and a non-transitory computer readable medium storing a program.

(ii) Related Art

It is considered that a device is operated by using biological information such as brain waves.

JP2015-211705A describes an apparatus that detects a brain wave biological signal from brain waves of a user, detects a surface brain wave biological signal from a surface myoelectric potential of the user, and calculates a control signal based on both the brain wave biological signals.

JP2016-067922A describes an apparatus that selectively operates a plurality of operated apparatuses according to an analysis result obtained by acquiring brain waves of a user and analyzing the brain waves.

SUMMARY

Incidentally, the device may not be accurately operated by using the biological information.

Aspects of non-limiting embodiments of the present disclosure relate to an information processing apparatus and a non-transitory computer readable medium storing a program that improve accuracy of an operation of a device in a case where the device is operated by using biological information.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided an information processing apparatus including a processor configured to associate information indicating a recognition result of a voice of a user uttered at a time at which the user manually operates a device, biological information other than the voice of the user, and manual operation information indicating a manual operation for the device with each other and operate the device based on the biological information in a subsequent operation.

BRIEF DESCRIPTION OF THE DRAWINGS

Exemplary embodiment(s) of the present invention will be described in detail based on the following figures, wherein.

DETAILED DESCRIPTION

Figure 1:
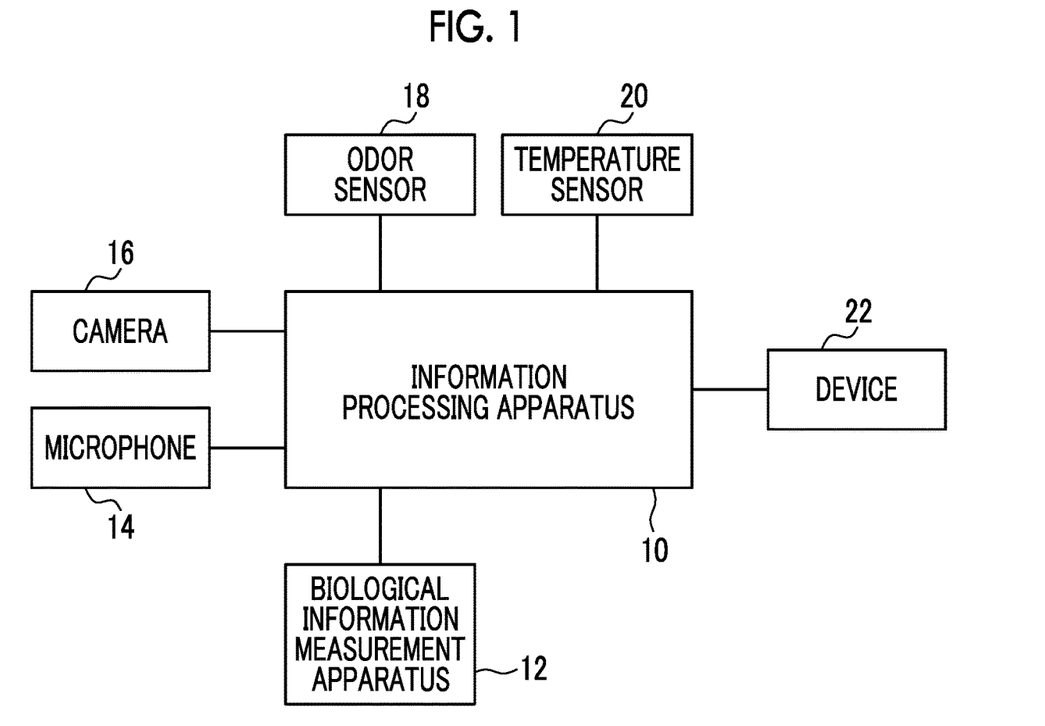
FIG. 1 is a block diagram showing a configuration of an information processing system according to an exemplary embodiment.

An information processing system according to an exemplary embodiment will be described with reference to FIG. 1. FIG. 1 shows an example of a configuration of the information processing system according to the present exemplary embodiment.

The information processing system according to the present exemplary embodiment includes an information processing apparatus 10, one or a plurality of biological information measurement apparatuses 12, one or a plurality of microphones 14, one or a plurality of cameras 16, one or a plurality of odor sensors 18, one or a plurality of temperature sensors 20, and one or a plurality of devices 22. The number of apparatuses and the number of sensors shown in FIG. 1 are merely examples, and the number of apparatuses and the number of sensors are not limited to the number of apparatuses and the number of sensors shown in FIG. 1. The information processing system may include other apparatuses (for example, external apparatuses such as servers) other than the apparatuses shown in FIG. 1.

The information processing apparatus 10, the biological information measurement apparatus 12, the microphone 14, the camera 16, the odor sensor 18, the temperature sensor 20, and the device 22 are configured to communicate with other apparatuses or sensors. The communication may be wired communication using a cable, or may be wireless communication. That is, the apparatuses and sensors may transmit and receive information to and from each other by being physically connected to other apparatuses or sensors by a cable, or may transmit and receive information to and from each other through wireless communication. For example, short-range wireless communication or Wi-Fi (registered trademark) is used as the wireless communication. Wireless communication according to standards other than the aforementioned wireless communication may be used. The short-range wireless communication is, for example, Bluetooth (registered trademark), radio frequency identifier (RFID), or NFC. The apparatuses may communicate with other apparatuses or sensors via a communication path such as a local area network (LAN) or the Internet.

The information processing apparatus 10 is, for example, a personal computer (hereinafter, referred to as a "PC"), a tablet PC, a smartphone, a mobile phone, or other apparatuses. The information processing apparatus 10 may be a terminal apparatus (for example, a tablet PC, a smartphone, or a mobile phone) that can be carried by a user, or may be an apparatus that is used while being installed on a table. The information processing apparatus 10 may be a smart speaker which has a communication function and includes a microphone and a speaker. The information processing apparatus 10 may be installed indoors (for example, a floor of a room, a ceiling, and a table), or may be installed outdoors. The information processing apparatus 10 may be a movable apparatus (for example, a self-propelled apparatus).

The biological information measurement apparatus 12 includes a sensor and an electrode, and is configured to measure biological information of the user. In a case where the plurality of biological information measurement apparatuses 12 is included in the information processing system, each biological information measurement apparatus 12 may measure different kinds of biological information items. Of course, a part or all of the biological information measurement apparatuses 12 may be configured to measure the same kind of biological information items. Each biological information measurement apparatus 12 may be configured to measure one kind of biological information items or may be configured to measure multiple kinds of biological information items.

The biological information measurement apparatus 12 transmits the biological information measured by the host apparatus to the information processing apparatus 10. The biological information measurement apparatus 12 may transmit the biological information to the information processing apparatus 10 whenever the biological information is measured, may store the biological information and may transmit the biological information to the information processing apparatus 10 at predetermined time intervals, or may transmit the biological information to the information processing apparatus 10 at a timing designated by the user. The biological information measurement apparatus 12 may receive the biological information measured by the other biological information measurement apparatus 12 from the other biological information measurement apparatus 12, and may transmit the biological information measured by the host apparatus and the biological information measured by the other biological information measurement apparatus 12 to the information processing apparatus 10.

The biological information measurement apparatus 12 may analyze the biological information measured by the host apparatus or the other biological information measurement apparatus, and may transmit information indicating an analysis result to the information processing apparatus 10. For example, the biological information measurement apparatus 12 may include a processor, and the processor may analyze the biological information. Of course, the analysis may be performed by the information processing apparatus 10.

The biological information measurement apparatus 12 includes a battery, and may be driven by a power supplied from the battery, or may be driven by receiving a power from the information processing apparatus 10.

The entire biological information measurement apparatus 12 is worn on the user, and the biological information measurement apparatus 12 may be a wearable apparatus that measures the biological information. For example, the biological information measurement apparatus 12 may be an apparatus worn on the head of the user, a hearable apparatus worn on the ear of the user, an apparatus (for example, wristwatch-type apparatus) worn on the arm, hand, wrist, or finger of the user, an apparatus worn on the neck of the user, or an apparatus worn on the trunk or legs of the user.

The biological information is various physiological information and anatomical information generated from a user who is a living body. The category of the concept of the biological information includes, for example, information indicating brain activity (for example, brain waves, brain blood flow, or brain magnetic field signal), a pulse rate, a blood pressure, a heart rate, an electrocardiographic waveform, electromyogram, eye movement, a body temperature, sweating, line of sight, voice, and user movement. The biological information items are merely examples, and other physiological information items or anatomical information items may be used as the biological information. The biological information measurement apparatus 12 may measure one biological information items among these biological information items, or may measure a plurality of biological information items.

The information processing apparatus 10 receives the biological information from the biological information measurement apparatus 12, and analyzes the biological information, stores the biological information, outputs the biological information, stores the information indicating the analysis result of the biological information, and outputs the information indicating the analysis result of the biological information. Of course, the biological information may be analyzed by the biological information measurement apparatus 12. The outputting of the biological information includes, for example, displaying of the biological information or outputting of the biological information as voice information. The outputting of information indicating the analysis result of the biological information includes, for example, displaying of the information indicating the analysis result or outputting of the analysis result as the voice information. The information processing apparatus 10 may transmit the biological information and the information indicating the analysis result to another apparatus.

The information processing apparatus 10 may include one or a plurality of biological information measurement apparatuses 12. That is, one or a plurality of biological information measurement apparatuses 12 may constitute one apparatus by being incorporated into the information processing apparatus 10. The entire information processing apparatus 10 including one or a plurality of biological information measurement apparatuses 12 may measure the biological information while being worn on the user. That is, the information processing apparatus 10 may be a wearable apparatus. For example, the information processing apparatus 10 may be an apparatus worn on the head of the user, a hearable apparatus worn on the ear of the user, an apparatus (for example, wristwatch-type apparatus) worn on the arm, hand, wrist, or finger of the user, an apparatus worn on the neck of the user, or an apparatus worn on the trunk or legs of the user.

Of course, the information processing apparatus 10 and the biological information measurement apparatus 12 may be separate apparatuses. For example, the information processing apparatus 10 may be a smart speaker, and the biological information measurement apparatus 12 may be a wearable apparatus worn by a user.

The microphone 14 is an apparatus that collects sound waves. Sound (for example, human voice or other sound) around the microphone 14 is input to the microphone 14, and sound data is generated by the microphone 14. The sound data indicating the sound input to the microphone 14 corresponds to an example of environment information indicating an environment around the microphone 14. Thus, the microphone 14 corresponds to an example of an environment information measurement apparatus. The sound data indicating the voice of the user input to the microphone 14 corresponds to an example of the biological information of the user. Thus, the microphone 14 corresponds to an example of a biological information measurement apparatus that measures the biological information of the user.

The camera 16 is an imaging apparatus. The surroundings and other locations of the information processing apparatus 10 are imaged by the camera 16, and image data indicating the surroundings and image data indicating other locations are generated. The image data may be moving image data or still image data. The image data imaged by the camera 16 corresponds to an example of environment information indicating an environment included in an imaging range of the camera 16. Thus, the camera 16 corresponds to an example of the environment information measurement apparatus. The image data indicating the user which is imaged by the user by using the camera 16 corresponds to an example of the biological information of the user. For example, the movement of the user or the body shape of the user detected from the image data corresponds to an example of the biological information of the user. Thus, the camera 16 corresponds to an example of the biological information measurement apparatus that measures the biological information of the user.

The odor sensor 18 is an apparatus that measures an odor around the odor sensor 18, and generates odor data indicating the measured odor. The odor data indicating the odor measured by the odor sensor 18 corresponds to an example of environment information indicating an environment around the odor sensor 18. Thus, the odor sensor 18 corresponds to an example of the environment information measurement apparatus. The odor data indicating the odor of the user measured by the odor sensor 18 corresponds to an example of the biological information of the user. Thus, the odor sensor 18 corresponds to an example of the biological information measurement apparatus that measures the biological information of the user.

The temperature sensor 20 is an apparatus that measures the temperature around the temperature sensor 20, and generates temperature data indicating the measured temperature. The temperature data indicating the temperature measured by the temperature sensor 20 corresponds to an example of environment information indicating an environment around the temperature sensor 20. Thus, the temperature sensor 20 corresponds to an example of the environment information measurement apparatus. The temperature data indicating the temperature of the user measured by the temperature sensor 20 corresponds to an example of the biological information of the user. Thus, the temperature sensor 20 corresponds to an example of the biological information measurement apparatus that measures the biological information of the user.

The camera 16, the odor sensor 18, and the temperature sensor 20 may not be included in the information processing system, and at least one thereof may be included in the information processing system. Other environment information measurement apparatuses (for example, a humidity sensor, an illuminance sensor, an atmospheric pressure sensor, or an infrared sensor) may be included in the information processing system. One or a plurality of environment information measurement apparatuses may be included in the information processing apparatus 10. For example, the camera 16 may be included in the information processing apparatus 10. The microphone 14 may be included in the information processing apparatus 10.

For example, the device 22 is a device such as a PC, a tablet PC, a smartphone, a mobile phone, a robot (for example, a humanoid robot, a non-human animal robot, a cleaning robot, and other robots), a projector, a display device such as a liquid crystal display, a recording device, a playback device, an imaging device such as a camera, a refrigerator, a rice cooker, a microwave oven, a coffee maker, a vacuum cleaner, a washing machine, an air conditioner, a lighting device, a watch, a surveillance camera, an automobile, a motorcycle, aircraft (for example, unmanned aircraft (for example, drone)), a game machine, a gas stove, an electronic bidet, a ventilation fan, a doorbell, an entrance monitor, an elevator, a door, a window, or various sensing devices (for example, a temperature sensor, a humidity sensor, a voltage sensor, and a current sensor). All devices may be included in the category of the device 22. For example, an information device, a video device, an audio device, and other devices may also be included in the category of the device 22 according to the present exemplary embodiment.

Figure 2:
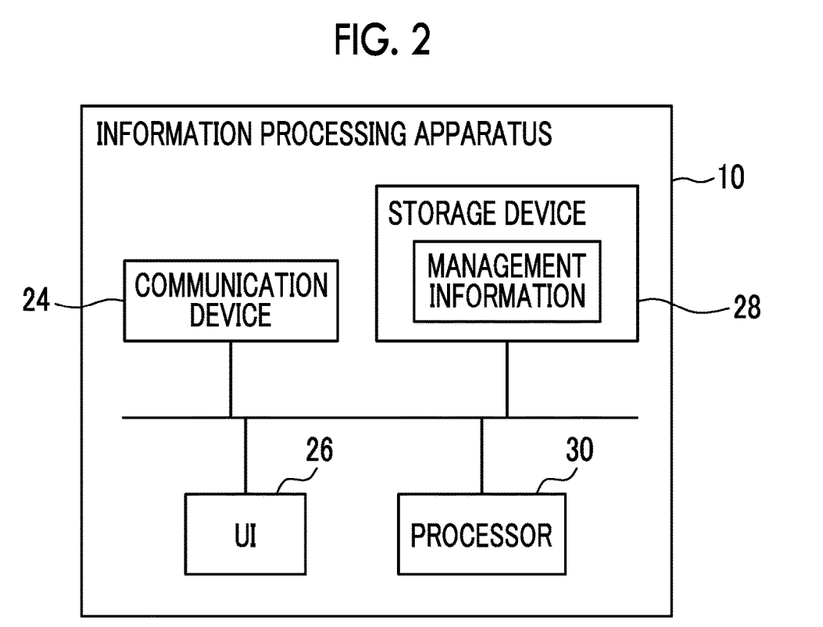
FIG. 2 is a block diagram showing a configuration of an information processing apparatus according to the present exemplary embodiment.

Hereinafter, a configuration of the information processing apparatus 10 will be described in detail.

The information processing apparatus 10 includes, for example, a communication device 24, a UI 26, a storage device 28, and a processor 30. The information processing apparatus 10 may include other configurations.

The communication device 24 is a communication interface, and has a function of transmitting data to other apparatuses and a function of receiving data transmitted from other apparatuses. The communication device 24 may have a wireless communication function or may have a wired communication function. The communication device 24 may communicate with other apparatuses by using, for example, short-range wireless communication, or may communicate with other apparatuses via a communication path such as a LAN or the Internet. The communication device 24 receives the biological information transmitted from the biological information measurement apparatus 12 by communicating with the biological information measurement apparatus 12. The communication device 24 may transmit control information for controlling an operation of the biological information measurement apparatus 12 to the biological information measurement apparatus 12. The communication device 24 receives the environment information transmitted from the environment information measurement apparatus by communicating with the environment information measurement apparatus. The communication device 24 may transmit control information for controlling an operation of the environment information measurement apparatus to the environment information measurement apparatus.

The UI 26 is a user interface, and includes a display device and an operation device. The display device is a liquid crystal display or an EL display. The operation device is a keyboard, input keys, or an operation panel. The UI 26 may be a UI of a touch panel serving as both the display device and the operation device. A microphone may be included in the UI 26, and a speaker that utters sound may be included in the UI 26.

The storage device 28 is a device constituting one or a plurality of storage regions for storing various data items. The storage device 28 is, for example, a hard disk drive, various memories (for example, RAM, DRAM, and ROM), other storage devices (for example, an optical disk), or a combination thereof. One or a plurality of storage devices 28 is included in the information processing apparatus 10.

Management information is stored in the storage device 28. The management information is information for managing biological information for operating the device 22. For example, for each operation of the device 22, manual operation information indicating a manual operation for the device 22, voice information indicating the operation of the device 22 by a voice, biological information other than the voice at a time at which the voice is uttered, and control information indicating the operation of the device 22 are registered in association with each other in advance in the management information. For each user, the manual operation information, the voice information, the biological information other than the voice, and the control information may be registered in association with each other in the management information.

The processor 30 is configured to operate the device 22 based on the biological information of the user. For example, in a case where a recognition result of the voice of the user uttered at a time at which the user manually operates the device 22 and the biological information of the user other than the voice are included an allowable range of the manual operation information indicating the manual operation for the device 22, the processor 30 operates the device 22 based on the biological information of the user in the subsequent operation. In the subsequent operation, the processor 30 may operate the device 22 based on a combination of the voice of the user and the biological information of the user other than the voice, or may operate the device 22 based on the biological information of the user other than the voice. For example, the processor 30 operates the device 22 according to the control information.

The voice of the user uttered at the time at which the user manually operates the device 22 is measured by the microphone 14, and the biological information of the user at this time is measured by the biological information measurement apparatus 12.

The processor 30 may recognize the device 22 manually operated by the user and the content of the operation by analyzing the image data imaged by the camera 16, and may recognize the device 22 manually operated by the user and the content of the operation by communicating with each device 22. For example, in a case where the host device is operated by the user, the device 22 transmits notification information which includes information indicating that the host device is operated by the user, information indicating the content of the operation, and information for identifying the host device to the information processing apparatus 10. The processor 30 recognizes the device 22 manually operated by the user and the content of the operation based on the notification information transmitted from the device 22.

For example, the processor 30 determines whether or not the recognition result of the voice of the user and the biological information of the user other than the voice are included in the allowable range of the manual operation information based on a waveform of the voice of the user and a waveform indicating the biological information other than the voice. For example, features of the waveform such as a shape, a peak, a cycle, or an amplitude of the waveform are used as elements for the determination. Further, the processor 30 may grasp a meaning content of speech of the user from the recognition result of the voice, and may determine whether or not the meaning content is included in the allowable range of the manual operation information.

For example, a case where the recognition result of the voice of the user uttered at the time at which the user manually operates the device 22 and the biological information of the user other than the voice are included in the allowable range of the manual operation information indicating the manual operation for the device 22 is a case where a difference between the recognition result of the voice of the user measured at the time at which the user manually operates the device 22 and the voice information registered in the management information is within a first allowable range and a difference between the biological information other than the voice of the user measured at the time at which the user manually operates the device 22 and the biological information registered in the management information is within a second allowable range. The first allowable range and the second allowable range are predetermined values, and may be changed by the user.

That is, in a case where the difference between the recognition result of the voice of the user measured at the time at which the user manually operates the device 22 and the voice information registered in the management information is within the first allowable range and the difference between the biological information other than the voice of the user measured at the time at which the user manually operates the device 22 and the biological information registered in the management information is within the second allowable range, the processor 30 operates the device 22 based on the biological information of the user in the subsequent operation.

The time at which the user manually operates the device 22 may be a point of time at which the device 22 is manually operated or a period including the point of time at which the device is manually operated. The period including the point of time at which the device is manually operated may be a period including a period after the point of time at which the device is manually operated, a period including a period before the point of time at which the device is manually operated, or a period including the periods before and after the point of time at which the device is manually operated. The period including the period after the point of time at which the device is manually operated is a period until a predetermined time elapses from the point of time at which the device is manually operated. The period including the period before the point of time at which the device is manually operated is a period from a predetermined point of time before the point of time at which the device is manually operated to the point of time at which the device is manually operated. The period including the periods before and after the point of time at which the device is manually operated is a period including both the period after the point of time at which the device is manually operated and the period before the point of time at which the device is manually operated. That is, the processor 30 determines whether or not voice and another biological information measured at the point of time at which the device is manually operated, voice and another biological information measured for the period including the period after the point of time at which the device is manually operated biological information, voice and another biological information measured for the period including the period before the point of time at which the device is manually operated, or voice and another biological information measured for the period including the periods before and after the point of time at which the device is manually operated are included in the allowable range of the manual operation information. The point of time at or the period during which the voice and another biological information used for the determination are measured may be determined by the user, or may be determined in advance.

In a case where the content of the operation manually performed includes a plurality of operations, a point of time at which a first operation included in the plurality of operations is performed may be the point of time at which the device is manually operated, a point of time at which an intermediate operation included in the plurality of operations is performed may be the point of time at which the device is manually operated, or a point of time at which the last operation included in the plurality of operations is performed may be the point of time at which the device is manually operated. For example, in a case where the identical operation is manually performed continuously such as a case where a set temperature of an air conditioner is changed by continuously pressing a button for changing the set temperature, any of a first point of time (for example, a first point of time at which the identical button continuously operated is pressed) of the continuous operation, an intermediate point of time (for example, an intermediate point of time at which the identical button continuously operated is pressed) of the continuous operation, and a last point of time (for example, a last point of time at which the identical button continuously operated is pressed) of the continuous operation is determined as the point of time at which the device is manually operated. Similarly, in a case where a plurality of different operations are manually performed continuously such as a case where a plurality of different buttons are continuously pressed, any of a first point of time (for example, a point of time at which a first button of the plurality of different buttons is pressed) of the continuous operation, an intermediate point of time (for example, an intermediate point of time at which a middle button (a button other than the first and last buttons) of the plurality of different buttons is pressed) of the continuous operation, and a last point of time (for example, a point of time at which a last button of the plurality of different buttons is pressed) of the continuous operation is determined as the point of time at which the device is manually operated. This point of time may be determined by the user, or may be determined in advance.

Processing for recognizing the voice of the user may be performed by the processor 30, or may be performed by an external apparatus such as a server. For example, a known technology is used as the processing for recognizing the voice. The processing for recognizing the voice may be performed by artificial intelligence.

In a case where the manual operation information, the voice information, the biological information other than the voice, and the control information are registered in association with each other in the management information for each user, the processor 30 may discriminate the voice for each user, and may operate the device 22 based on the biological information.

For example, a brain machine interface may be constructed by the biological information measurement apparatus 12 and the information processing apparatus 10 that measure the brain activity. A method of the brain machine interface may be an invasive method, or may be a non-invasive method. In this case, the processor 30 operates the device 22 based on the brain activity (for example, brain waves) of the user. In order to operate the device 22, the processor 30 may extract feature components from the brain waves, and may operate the device 22 based on the extracted component. In order to extract the feature components from the brain waves, a fast Fourier transform (FFT), a wavelet transform (WT), a time frequency distribution (TFD), eigenvector methods (EM), an autoregressive model (ARM) may be used. As a method for linking the brain waves and the operation of the device 22 by using a feature vector obtained by the extraction of the features, for example, independent component analysis (ICA), a k-average method, a support vector machine (SVM), or a convolutional neural network may be used.

The processor 30 is configured to control the operations of the units of the information processing apparatus 10. The processor 30 may include a memory.

Hereinafter, the information processing system according to the present exemplary embodiment will be described in detail in conjunction with specific examples.

Figure 3:
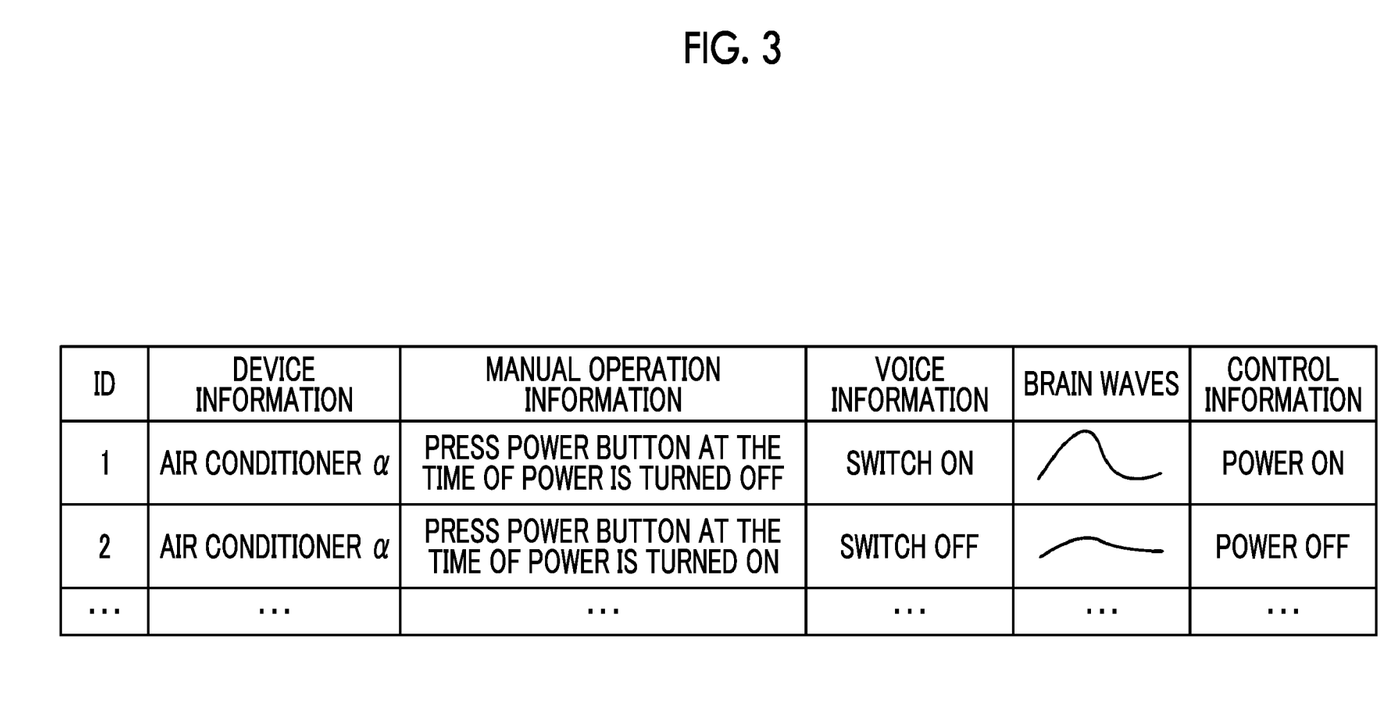
FIG. 3 is a diagram showing a management table.

FIG. 3 shows an example of a management table which is an example of management information. Data items of the management table are stored in the storage device 28. The data items of the management table may be stored in an external apparatus such as a server without being stored in the storage device 28.

In the management table, for each operation of the device 22, an ID, device information, the manual operation information, the voice information, the brain waves which are an example of the biological information other than the voice, and the control information are associated in advance. The management table shown in FIG. 3 is not a management table reflecting specific biological information items of individual users, but is a default management table created in advance. Here, the brain waves are used as the biological information other than the voice, but the biological information other than the brain waves may be used as long as the biological information other than the voice is used.

The ID is information for managing the operation of the device 22. The device information is information for identifying the device 22 to be operated, and is, for example, a name, a device ID, or a model number of the device 22. The manual operation information is information indicating the manual operation of the user for the device 22. The voice information is information indicating the operation of the device 22 by a voice. The voice information may be voice data (for example, a waveform indicating the voice) indicating the operation of the device 22 by a voice, or information indicating the recognition result of the voice. The information indicating the recognition result of the voice may be information indicating the voice with a text string, information indicating the feature of the voice, or information indicating the meaning content indicated by the voice. Specifically, the voice information is information indicating voice assumed to be uttered from the user at the time at which the user manually performs the operation indicated by the manual operation information for the device 22. The brain waves are the biological information indicating the operation for the device 22. Specifically, the brain waves are the biological information assumed to be emitted from the user at the time at which the operation is performed for the device 22. The brain waves (that is, the waveform) may not be registered in the management table, and the information indicating the operation specified by analyzing the brain waves may be registered in the management table. The control information is information indicating the operation of the device 22.

Hereinafter, a specific example will be described.

The information associated with an ID "1" is information regarding an operation of "air conditioner α" which is an example of the device 22.

The manual operation information associated with the ID "1" is information indicating a manual operation of "pressing a power button at a time at which a power of "air conditioner α" is turned off". In a case where the power of "air conditioner α" is turned on at the time at which the power of "air conditioner α" is turned off, it is assumed that the user turns on the power button of "air conditioner α". This manual operation information is information indicating the manual operation. The power button of "air conditioner α" is provided on, for example, a remote controller for operating "air conditioner α".

The voice information associated with the ID "1" is information indicating a voice "switch on". This voice information may be voice data (for example, a waveform indicating the voice) indicating a voice "switch on", or may be information indicating a text string "switch on". The voice information indicating the voice "switch on" is information indicating the voice assumed to be uttered from the user at a time at which the user presses the power button in a case where the power of "air conditioner α" is turned off. That is, at a time at which the user presses the power button in a case where the power of "air conditioner α" is turned off, it is assumed that the user utters the voice indicating "switch on".

The brain waves associated with the ID "1" are brain waves indicating an operation of turning on the power of "air conditioner α". Specifically, the brain waves are brain waves assumed to be emitted from the user at a time at which the user turns on the power in a case where the power of "air conditioner α" is turned off. That is, at a time at which the user turns on the power in a case where the power of "air conditioner α" is turned off, it is assumed that the brain waves associated with the ID "1" are emitted from the user.

The control information associated with the ID "1" is information indicating an operation of turning on the power of "air conditioner α".

For example, it is assumed that at the time at which the power of "air conditioner α" is turned off, the user presses the power button of "air conditioner α" while producing the voice. The voice is measured by the microphone 14. The biological information measurement apparatus 12 measures the brain waves emitted from the user at a time at which the user presses the power button of "air conditioner α" while producing the voice.

The operation of pressing the power button of "air conditioner α" at the time at which the power of "air conditioner α" is turned off is the operation of ID "1". For example, in a case where "air conditioner α" which is the device 22 is manually operated by the user, the host device transmits the notification information including the information indicating that the host device is manually operated by the user, the information indicating the content of the operation (for example, the operation of turning on the power), and the information for identifying "air conditioner α" which the host device to the information processing apparatus 10. The processor 30 recognizes that "air conditioner α" is manually operated by the user based on the notification information transmitted from "air conditioner α", and further recognizes that the content of the operation is to turn on the power. That is, the processor 30 recognizes that the operation of ID "1" is performed. In a case where a scene in which the user performs the operation of turning on the power by using the remote controller of "air conditioner α" is imaged by the camera 16, the processor 30 may recognize that "air conditioner α" is operated by the user by analyzing the imaged image data, and may recognize that the content of the operation is to turn on the power.

In a case where the recognition result of the voice uttered by the user at a time at which the power button of "air conditioner α" is pressed is "switch on", the recognition result of the voice matches the voice information associated with the ID "1". In a case where the brain waves measured at this time match the brain waves associated with the ID "1", the processor 30 may operate "air conditioner α" based on a combination of the voice and the brain waves of the user, or may operate "air conditioner α" based on the brain waves of the user in the subsequent operation.

It is estimated that an intention of the user is accurately reflected on the content of the voice uttered by the user at the time of operating the device 22. That is, at a time at which the user operates the device 22, since it is considered that the user does not bother to lie, it is assumed that the intention of the user is accurately reflected on the content of the voice uttered by the user at the time of operating the device 22. For example, at a time at which the user manually turns on the power, it is not considered that the user speaks contrary to the content of the operation (for example, a speech "OFF"). Therefore, it is estimated that the intention of the user is accurately reflected on the content of the voice uttered by the user at the time of operating the device 22 and the intention of the user is accurately reflected on the biological information (for example, brain waves) other than the voice uttered by the user at this time. Therefore, it is possible to improve the accuracy of the operation for the device 22 by using the voice.

For example, in the subsequent operation, at the time at which the power of "air conditioner α" is turned off, in a case where the brain waves associated with the ID "1" are measured from the user and the voice indicated by the voice information associated with the ID "1" is measured from the user, the processor 30 turns on the power of "air conditioner α" according to the control information associated with the ID "1". For example, the processor 30 turns on the power of "air conditioner α" by transmitting the control information instructing to turn on the power to "air conditioner α". In a case a difference between the brain waves measured from the user and the brain waves associated with the ID "1" is within an allowable range and a difference between the voice measured from the user and the voice indicated by the voice information associated with the ID "1" is within the allowable range, the processor 30 may turn on the power of "air conditioner α" according to the control information associated with the ID "1". It is estimated that the operation is easily reflected on the brain waves than by producing the voice indicating the operation at the time of operating the device 22 as compared to a case where the voice is not uttered. Therefore, it is possible to improve the accuracy of the operation for the device 22 the producing the voice indicating the operation at the time of operating the device 22 as compared to the case where the voice is not uttered.

As another example, in the subsequent operation, at the time at which the power of "air conditioner α" is turned off, in a case where the brain waves associated with the ID "1" are measured from the user, the processor 30 may turn on the power of "air conditioner α" according to the control information associated with the ID "1". In a case where the difference between the brain waves measured from the user and the brain waves associated with the ID "1" is within the allowable range, the processor 30 may turn on the power of "air conditioner" according to the control information associated with the ID "1".

In a case where the difference between the recognition result of the voice uttered by the user at the time at which the power button of "air conditioner α" is pressed and the voice information "switch on" associated with the ID "1" is within the first allowable range and the difference between the brain waves measured at this time and the brain waves associated with the ID "1" is within the second allowable range, the processor 30 may perform the operation of turning on the power of "air conditioner α" based on the combination of the voice and the brain waves of the user, and may perform the operation of turning on the power of "air conditioner α" based on the brain waves of the user in the subsequent operation.

For example, in a case where the recognition result of the voice uttered by the user at the time at which the power button of "air conditioner α" is pressed is "on", the recognition result "on" is different from the voice information "switch on" associated with the ID "1". In this case, the processor 30 determines whether or not the difference between the recognition result "on" and the voice information "switch on" associated with the ID "1" is within the first allowable range. For example, the processor 30 compares a text string "on" indicating the voice which is the recognition result of the voice with a text string "switch on" indicating the voice information "switch on" associated with the ID "1", and determines whether or not the difference between these text strings is within the first allowable range. For example, the processor 30 may recognize the meaning content indicated by each text string by analyzing each text string, and determine whether or not the difference between the meaning contents is within the first allowable range. The processor 30 may analyze the text string by using, for example, natural language processing, morphological element analysis, syntax analysis, and statistical natural language processing. The analysis of the text string and the comparison of the recognition results of the voices may be performed by artificial intelligence. For example, since the recognition result "on" of the voice uttered by the user has a meaning of turning on the power, the processor 30 determines that the difference between the recognition result "on" of the voice and the voice information "switch on" associated with the ID "1" is within the first allowable range.

As another example, the processor 30 may compare the waveform of the voice which is the recognition result of the voice uttered by the user with the waveform indicated by the voice information associated with the ID "1". Specifically, the processor 30 may extract features such as a shape, a peak, a cycle, and an amplitude of the waveform from each waveform, may compare the features of both the waveforms, and may determine whether or not the difference between the features of both the waveforms is within the first allowable range.

The processor 30 may calculate a degree of similarity between both the waveforms, and may determine whether or not the degree of similarity is equal to or greater than a first threshold value. The first threshold value is a threshold value corresponding to the first allowable range. In a case where the degree of similarity between both the waveforms is equal to or greater than the first threshold value, the processor 30 determines that both the waveforms are similar, and determines that the difference between the recognition result of the voice uttered by the user and the voice information associated with the ID "1" is within the first allowable range. A known technology may be used in order to calculate the degree of similarity between the waveforms.

In a case where the brain waves measured from the user at the time at which the power button of "air conditioner α" is pressed is different from the brain waves associated with the ID "1", the processor 30 determines whether or not the difference between the measured brain waves and the brain-waves associated with the ID "1" is within the second allowable range. Specifically, the processor 30 extracts the features such as the shape, the peak, the cycle, and the amplitude of the brain waves from each of the brain waves measured from the user and the brain waves associated with the ID "1", compares the features of the waveforms, and determines whether or not the difference between the features of both the waveforms is within the second allowable range.

The processor 30 may calculate the degree of similarity between both the waveforms, and may determine whether or not the degree of similarity is equal to or greater than a second threshold value. The second threshold value is a threshold value corresponding to the second allowable range. In a case where the degree of similarity between both the waveforms is equal to or greater than the second threshold value, the processor 30 determines that both the waveforms are similar, and determines that the difference between the brain waves measured from the user and the brain waves associated with the ID "1" is within the second allowable range.

In a case where the difference between the recognition result of the voice uttered by the user and the voice information associated with the ID "1" is within the first allowable range and the difference between the brain waves measured from the user and the brain waves associated with the ID "1" is within the second allowable range, the processor 30 performs the operation of turning on the power of "air conditioner α" based on the combination of the voice and the brain waves of the user, or may perform the operation of turning on the power of "air conditioner α" based on the brain waves of the user in the subsequent operation.

For example, in the subsequent operation, at the time at which the power of "air conditioner α" is turned off, in a case where the voice of which the difference from the voice indicated by the voice information associated with the ID "1" is within the first allowable range is measured from the user and the brain waves of which the difference from the brain waves associated with the ID "1" is within the second allowable range is measured from the user, the processor 30 turns on the power of "air conditioner α" according to the control information associated with the ID "1".

As another example, in the subsequent operation, at the time at which the power of "air conditioner α" is turned off, in a case where the brain waves of which the difference from the brain waves associated with the ID "1" is within the second allowable range is measured from the user, the processor 30 turns on the power of "air conditioner α" according to the control information associated with the ID "1".

Similarly to the operation of ID "1", for operations other than the operation of ID "1", in a case where the recognition result of the voice of the user and the brain waves are included in the allowable range of the manual operation information, the operation is performed based on the combination of the voice and the brain waves or based on the brain waves in the subsequent operation.

In addition, in a case where the device 22 is operated based on the combination of the voice and the brain waves of the user and the number of times of the operation is equal to or greater than a threshold value, the processor 30 may operate the device 22 based on only the brain waves of the user in the subsequent operation. As another example, in a case where a success rate of the operation based on the combination of the voice and the brain waves of the user is equal to or greater than a threshold value, the processor 30 may operate the device 22 based on only the brain waves of the user in the subsequent operation.

As stated above, the processor 30 may stepwisely reduce information used for operating the device 22. Specifically, in a first stage, the processor 30 operates the device 22 based on a combination of the manual operation of the user, the voice, and the biological information (for example, brainwaves) other than the voice. In a second stage, the processor 30 operates the device 22 based on a combination of the voice of the user and the biological information other than the voice. In a third stage, the processor 30 operates the device 22 based on the biological information of the user other than the voice. In a case where the success rate of the operation at the first stage is equal to or greater than the threshold value and the operation at the second stage is performed and the success rate of the operation at the second stage is equal to or greater than the threshold value, the operation at the third stage may be performed.

At the time at which the user manually operates the device 22, the user may utter the voice indicating the device information for identifying the device 22 to be operated. The voice is measured by the microphone 14, and the processor 30 specifies the device 22 to be operated by analyzing the voice. The processor 30 searches for the device 22 to be operated in the management table, and controls the operation for the device 22. For example, in a case where the user utters the voice indicating "air conditioner α" while pressing the power button of "air conditioner α" at the time at which the power of "air conditioner α" is turned off, the processor 30 specifies that the device 22 to be operated is "air conditioner α" based on the voice. Since the operation of pressing the power button of "air conditioner α" at the time at which the power of "air conditioner α" is turned off is the operation associated with the ID "1", the processor 30 determines whether or not the recognition result of the voice of the user and the brain waves are included in the allowable range of the manual operation information associated with the ID "1".

At the time at which the user operates the device 22 based on the brain waves, the user may utter the voice indicating the device information for identifying the device 22 to be operated. The processor 30 specifies the device 22 to be operated by the brain waves by analyzing the voice. The processor 30 searches for the device 22 to be operated in the management table by the brain waves, and compares the brain waves associated with the device 22 with the brain waves measured from the user. In a case where the difference between both the brain waves is within the second allowable range, the processor 30 operates the device 22 according to the control information associated with the brain waves associated with the device 22. For example, at the time at which the user turns on "air conditioner α" by the brain waves, in case where user utters the voice indicating "air conditioner α", the processor 30 specifies that the device 22 measured by the brain waves is "air conditioner α" based on the voice. In the example shown in FIG. 3, the operation associated with the ID "1" and the operation associated with an ID "2" are registered, as the operation for "air conditioner α", in the management table. The processor 30 compares the brain waves associated with the ID "1" and the ID "2" with the brain waves measured from the user. In a case where the difference between the brain waves associated with the ID "1" and the brain waves measured from the user is within the second allowable range and the difference between the brain waves associated with the ID "2" and the brain waves measured from the user is not within the second allowable range, the processor 30 operates "air conditioner α" according to the control information associated with the ID "1". In this case, the processor 30 turns on the power of "air conditioner α". Meanwhile, in a case where the difference between the brain waves associated with the ID "1" and the brain waves measured from the user is not within the second allowable range and the difference between the brain waves associated with the ID "2" and the brain waves measured from the user is within the second allowable range, the processor 30 operates "air conditioner α" according to the control information associated with the ID "2". In this case, the processor 30 turns off the power of "air conditioner α".

Figure 4:
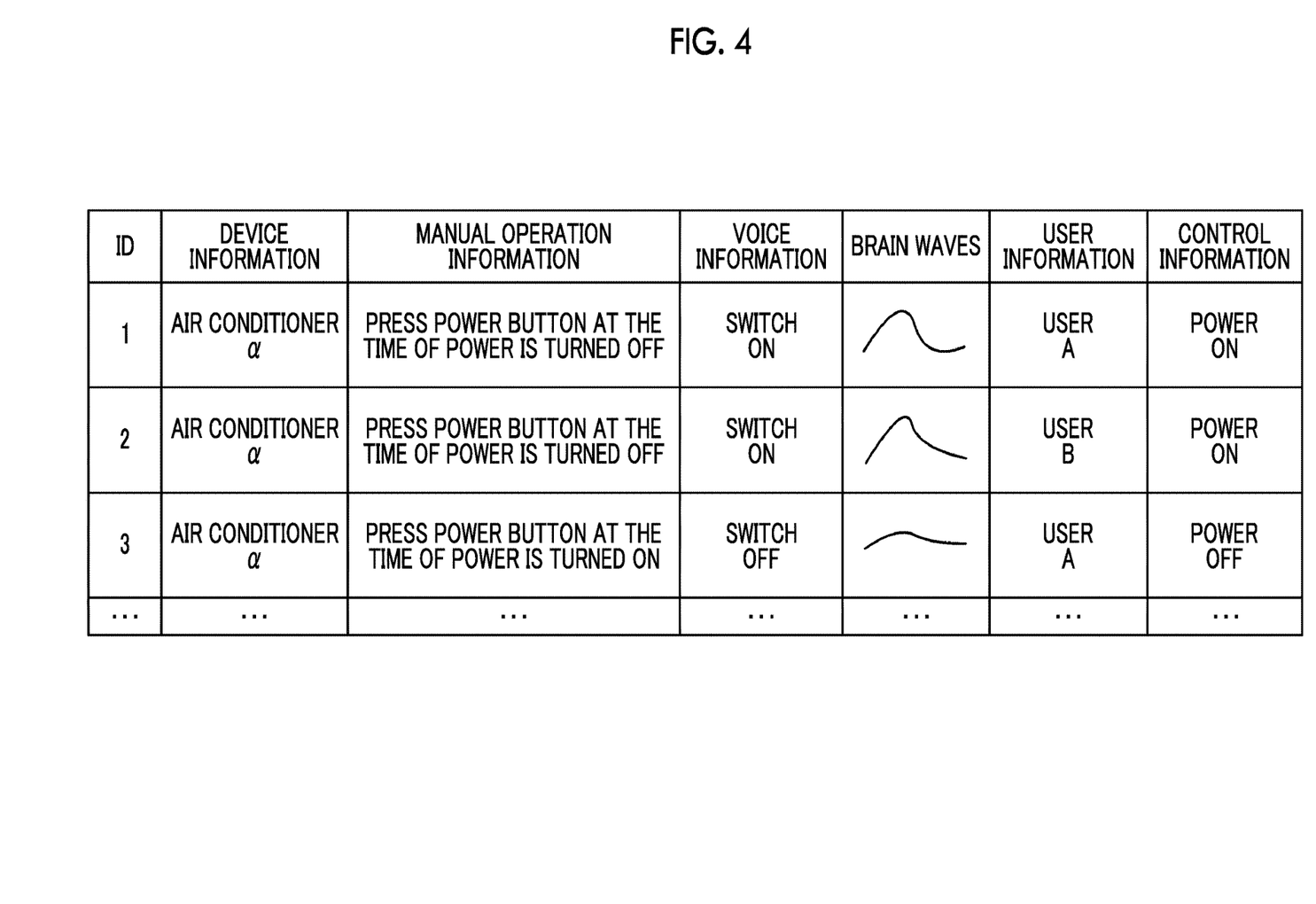
FIG. 4 is a diagram showing a management table.

The manual operation information, the voice information, the brain waves, and the control information may be registered in association with each other in the management table for each user. Specifically, specific brain waves of individual users may be registered in the management table.

FIG. 4 shows a management table in which specific brain waves of individual users are registered. In the management table shown in FIG. 4, the ID, the device information, the manual operation information, the voice information, the brain waves which are an example of the biological information other than voice, and the control information are associated with user information for each operation of the device 22. Regarding the identical operation, the brain waves of each user are registered in the management table. The user information is information (for example, a user name or a user ID) for identifying the user. The user information may not be registered in the management table.

For example, it is assumed that a user A utters voice indicating "switch on" while pressing the power button of "air conditioner α" at the time at which the power of "air conditioner α" is turned off. At the time at which "air conditioner α" is operated by the user A in this manner, "air conditioner α" transmits the notification information including the information indicating that the host device is manually operated by the user, the information indicating the content of the operation (for example, the operation of turning on the power by pressing the power button at the time of turning off the power, and the information for identifying "air conditioner α" which is the host device to the information processing apparatus 10. The processor 30 recognizes that "air conditioner α" is operated by the user based on the notification information transmitted from "air conditioner α", and further recognizes that the content of the operation indicating that the power is turned on by pressing the power button at the time of turning off the power. In a case where a scene in which the user A performs the operation of turning on the power by using the remote controller of "air conditioner α" is imaged by the camera 16, the processor 30 may recognize that "air conditioner α" is operated by the user by analyzing the imaged image data, and may recognize that the content of the operation is to turn on the power by pressing the power button at the time of turning off the power.

The voice indicating "switch on" is measured by the microphone 14. The brain waves emitted from the user A at the time at which the user A presses the power button of "air conditioner α" while emitting the voice is measured by the biological information measurement apparatus 12.

The processor 30 registers the device information for identifying "air conditioner α" which is the device 22 operated by the user, the manual operation information indicating that the power button is pressed at the time of turning off the power, the voice information indicating the voice "switch on" measured by the microphone 14, the brain waves measured by the biological information measurement apparatus 12, and the control information indicating the operation to turn on the power in association with each other in the management table. The registered brain waves are the brain waves measured from the user A. The voice information may be voice data indicating the voice, or may be information indicating the recognition result of the voice. The voice data is data indicating the voice of the user A. In the example shown in FIG. 4, these information items are registered in association with the ID "1" in the management table. The brain waves associated with the ID "1" are the brain waves measured from the user A.

After each information is registered in the management table, the processor 30 operates "air conditioner α" based on the combination of the voice and the brain waves of the user or based on the brain waves of the user. Specifically, at the time at which the power of "air conditioner α" is turned off, in a case where the voice indicated by the voice information associated with the ID "1" is measured from the user and the brain waves associated with the ID "1" are measured from the user, the processor 30 turns on the power of "air conditioner α" according to the control information associated with the ID "1". At the time at which the power of "air conditioner α" is turned off, in a case where the voice of which the difference from the voice indicated by the voice information associated with the ID "1" is within the first allowable range is measured from the user and the brain waves of which the difference from the brain waves associated with the ID "1" is within the second allowable range are measured from the user, the processor 30 may turn on the power of "air conditioner α" according to the control information associated with the ID "1". At the time at which the power of "air conditioner α" is turned off, in a case where the brain waves associated with the ID "1" are measured from the user, the processor 30 may turn on the power of "air conditioner" according to the control information associated with the ID "1". At the time at which the power of "air conditioner α" is turned off, in a case where the brain waves of which the difference from the brain waves associated with the ID "1" is within the second allowable range are measured from the user, the processor 30 may turn on the power of "air conditioner α" according to the control information associated with the ID "1". In a case where the user information for identifying the user A is not associated with the ID "1" and the brain waves and the voice indicated by the voice information associated with the ID "1" are measured from another user other than the user A or the brain waves associated with the ID "1" are measured, the processor 30 turns on the power of "air conditioner α" according to the control information associated with the ID "1".

The user information for identifying the user A may be registered in association with the ID "1" in the management table. For example, after each information associated with the ID "1" is registered in the management table, the user may associate the user information with the ID "1" by editing the management table. As another example, in a state in which only the user A is logged in to the information processing apparatus 10, in a case where the voice and the brain waves are measured, the processor 30 recognizes that the measured voice and brain waves are the voice and brain waves of the user A, and may associate the user information for identifying the user A being logged in with the ID "1". In a case where the user to be registered in the user information is set as "user A" to the information processing apparatus 10, the processor 30 may recognize that the measured voice and brain waves are the voice and brain waves of the user A, and may associate the user information for identifying the user A to be registered with the ID "1". For example, the user to be registered in the user information is set in the information processing apparatus 10 by the user.

In a case where the user information for identifying the user A is registered in association with the ID "1" in the management table and the combination of the brain waves and the voice indicated by the voice information associated with the ID "1" are measured from the user A, the processor 30 turns on the power of "air conditioner α" according to the control information associated with the ID "1". This processing corresponds to the processing at the above-described second stage.

For example, in a state in which only the user A is logged in to the information processing apparatus 10 and the combination of the brain waves and the voice indicated by the voice information associated with the ID "1" is measured from the user A, the processor 30 turns on the power of "air conditioner α" according to the control information associated with the ID "1". Specifically, at the time at which only the user A is logged in to the information processing apparatus 10, in a case where the voice is measured by the microphone 14 and the brain waves are measured by the biological information measurement apparatus 12, the processor 30 searches for the combination of the voice information and the brain waves registered in association with the user information for identifying the user A being logged in the management table. In the example shown in FIG. 4, since the combination of the voice information and the brain waves associated with the ID "1" and the combination of the voice information and the brain waves associated with an ID "3" are registered in association with the combination of the voice information and the brain waves of the user A in the management table, the combination thereof is searched for. In a case where the combination of the measured voice and brain waves matches the combination of the brain waves and the voice indicated by the voice information associated with the ID "1" or in a case where the difference between the measurement voice and the voice indicated by the voice information associated with the ID "1" is within the first allowable range and the difference between the measured brain waves and the brain waves associated with the ID "1" is within the second allowable range, the processor 30 turns on the power of "air conditioner α" according to the control information associated with the ID "1". In a case where the combination of the measured voice and the brain waves matches the combination of the brain waves and the voice indicated by the voice information associated with the ID "3" or in a case where the difference between the measured voice and the voice indicated by the voice information associated with the ID "3" is within the first allowable range and the difference between the measured brain waves and the brainwaves associated with the ID "3" is within the second allowable range, the processor 30 turns off the power of "air conditioner α" according to the control information associated with the ID "3".

As another example, in a state in which the user who operates the device 22 is set as "user A" to the information processing apparatus 10, in a case where the combination of the brain waves and the voice indicated by the voice information associated with the ID "1" is measured from the user A, the processor 30 may turn on the power of "air conditioner α" according to the control information associated with the ID "1". Specifically, in a state in which the user who operates the device 22 is set as "user A" to the information processing apparatus 10, in a case where the voice is measured by the microphone 14 and the brain waves are measured by the biological information measurement apparatus 12, the processor 30 searches for the combination of the voice information and the brain waves registered in association with the user information for identifying the user A that is the user who operate the device 22 in the management table. In a case where the combination of the measured voice and brain waves matches the combination of the brain waves and the voice indicated by the voice information associated with the ID "1" or in a case where the difference between the measurement voice and the voice indicated by the voice information associated with the ID "1" is within the first allowable range and the difference between the measured brain waves and the brain waves associated with the ID "1" is within the second allowable range, the processor 30 turns on the power of "air conditioner α" according to the control information associated with the ID "1". The user who operates the device 22 is set to the information processing apparatus 10 by the user, for example.

As another example, in a case where the user information for identifying user A is registered in association with the ID "1" in the management table and the brain waves associated with the ID "1" are measured from the user A or the brain waves of which the difference from the brain waves associated with the ID "1" is within the second allowable range are measured, the processor 30 may turn on the power of "air conditioner α" according to the control information associated with the ID "1". This processing corresponds to the processing at the above-described third stage.

Similarly to the user A, each information is registered in the management table for a user other than the user A. For example, each information associated with the ID "2" is information regarding the operation at the time at which a user B turns on the power of "air conditioner α". Each information associated with the ID "3" is information regarding the operation at the time at which the user A turns off the power of "air conditioner α".

The processor 30 may discriminate the voice for each user, and may operate the device 22 based on the combination of the voice and the biological information other than the voice or based on the biological information other than the voice. For example, the processor 30 discriminates the user who utters the voice based on the voice measured by the microphone 14. For example, the voice data indicating the voice of the user and the user information for identifying the user are associated with each other, and may be stored in advance in the storage device 28 or the server for each user. In a case where the voice is measured by the microphone 14, the processor 30 searches for user identification information associated with the voice data indicating the measured voice, and specifies the user who utters the voice. The processor 30 specifies the operation with which the user information of the user who utters the voice is associated in the management table shown in FIG. 4, and operates the device 22 based on the combination of the brain waves and the voice information indicating the voice of the user or the brain waves of the user.

While the user is sleeping, the processor 30 may stop the operation of the device 22 using the biological information. The processor 30 determines whether or not the user is sleeping based on the biological information measured from the user by using, for example, a known technology. It is known that a sleep state of a person can be grasped based on the type, intensity, and transition of the brain waves. Sleep states are classified into, for example, REM sleep, non-REM sleep, and awakening. Of course, this classification is merely an example, and another classification may be used. Here, for example, in a case where the sleep state of the user is the REM sleep or the non-REM sleep, the state of the user is a sleeping state, and in a case where the sleep state of the user is awakening, the state of the user is a non-sleeping state. The processor 30 determines the sleep state of the user based on the type, intensity, and transition of the measured brain waves by using a known technology.

It is known that the brain waves during falling asleep are generated in the order of β waves, α waves, θ waves, and δ waves. In a case where the user lies down and closes the eyes of the user, the user relaxes from a state in which the β waves are generated, and the α waves are generated. From this stage, the θ waves are generated in a case where consciousness fades, and the δ waves are generated in a case where sleep is deep. The processor 30 determines the sleep state of the user by analyzing the brain waves generated in this manner.

An acceleration sensor which is an example of the biological information measurement apparatus 12 may be worn on the user, and an acceleration of the user, that is, movement may be measured. The processor 30 may recognize the sleep state of the user based on the magnitude of the acceleration and the amount of change. The processor 30 may grasp the sleep state of the user based on a pulse rate and a blood pressure of the user.

While the user is sleeping, the processor 30 may stop the processing for associating the voice information and the biological information of the user. For example, even though the voice or the brain waves are measured from the sleeping user, the processor 30 does not associate the voice information with the brain waves, and does not register the voice information and the brain waves in the management table.

In a case where voices of the plurality of users or voices of a predetermined number of users or more are measured by the microphone 14, the processor 30 may stop the operation of the device 22 using the biological information, may permit only the operation of the application based on the biological information, or may stop the association between the voice information and the biological information.

In a case where the device 22 is operated based on the combination of the voice of the user and the biological information (for example, brain waves) other than the voice and the voice other than the authenticated user is measured by the microphone 14, the processor 30 may stop the operation of the device 22 based on the combination of the voice and the biological information other the voice and the operation of the device 22 based on the biological information other than voice. The authenticated user is, for example, a user who is authenticated by the information processing apparatus 10 or another apparatus such as an authentication server. For example, a user who is logged in to the information processing apparatus 10 or a user who is permitted to operate the device 22 by using the biological information corresponds to an example of the authenticated user.

In a case where the device 22 is operated based on the combination of the voice of the user and the biological information other than the voice or based on the biological information other than the voice, the processor 30 may notify the user the content of the operation before the device 22 is operated. In a case where the consent of the user is obtained, the processor 30 may operate the device. For example, the processor 30 may notify the user of the operation content with voice, or may display the information indicating the content of the operation on the display unit of the UI 26. The consent of the user may be given by the biological information of the user. For example, in a case where the brain waves indicating the consent are measured by the biological information measurement apparatus 12, the processor 30 operates the device 22.

When the device 22 to be operated is not present within an operation range, the processor 30 may output a warning. For example, the processor 30 may display information indicating the warning on the display unit of the UI 26, or may produce a warning sound. The operation range is, for example, a range within a predetermined distance from a predetermined position with the predetermined position as reference. The predetermined position may be a position of the user, may be a position at which the information processing apparatus 10 is installed, or may be any position designated by the user. For example, the position of the user is specified by specifying the position of the terminal apparatus (for example, a smartphone) carried by the user by the Global Positioning System (GPS). The position of the information processing apparatus 10 may be set to the information processing apparatus 10, or may be specified by the GPS.

In a case where the biological information indicating an operation instruction for each of the plurality of devices 22 is received, the processor 30 may operate each device 22 by transmitting the control information corresponding to the biological information to each device 22.

Hereinafter, modification examples will be described. In the modification example, the processor 30 operates the device 22 based on the biological information generated from the user who receives an external stimulus. The processor 30 detects the external stimulus based on the environment information measured by the environment information measurement apparatus, and determines whether or not the user receive the external stimulus. The processor 30 determines whether or not the biological information measured from the user is biological information generated from the user who receives the external stimulus. In a case where the biological information measured from the user is the biological information generated from the user who receives the external stimulus, the processor 30 operates the device 22 based on the biological information. The environment information measurement apparatus is, for example, the microphone 14, the camera 16, the odor sensor 18, and the temperature sensor 20. Sensors other than the aforementioned sensors may be used as the environment information measurement apparatus. For example, the processor 30 determines whether or not the receives the external stimulus based on at least one data item of the sound data measured by the microphone 14, the image data imaged by the camera 16, the odor data measured by the odor sensor 18, or the temperature data measured by the temperature sensor 20. The processor 30 may determine whether or not the user receives the external stimulus based on data other than the aforementioned data items.

For example, specific environment information is measured, and biological information measured from the user after the specific environment information is measured is estimated to be biological information generated from the user who receives the external stimulus. In this case, an environment indicated by the specific environment information corresponds to an example of the external stimulus. For example, the biological information measured from the user for a time until a predetermined time elapses after a point of time at which the specific environment information is measured is estimated to be biological information generated from the user who receives the external stimulus. The environment indicated by the specific environment information is, for example, an environment related to the operation of the device 22. For example, in a case where the specific environment information related to the operation of the device 22 is measured, the processor 30 operates the device 22 based on the biological information measured from the user after the specific environment information is measured.

Hereinafter, the modification examples will be described in detail.

Modification Example 1

In Modification Example 1, the specific voice measured by the microphone 14 corresponds to an example of the external stimulus, and the voice data indicating the specific voice corresponds to an example of the specific environment information. The biological information is, for example, the brain waves. The specific voice is, for example, a voice (for example, conversation) related to the operation of the device 22. The biological information measured from the user after the voice data indicating the specific voice is measured is estimated to be the biological information generated from the user who receives the specific voice which is the external stimulus. In this case, the processor 30 operates the device 22 based on the biological information generated from the user who receives the specific voice. That is, the processor 30 operates the device 22 based on the biological information generated from the user by hearing the specific voice. For example, the biological information measured from the user for a time until a predetermined time elapses after a point of time at which the specific voice is measured is estimated to be the biological information generated from the user who hears the specific voice which is the external stimulus.

For example, a voice of a conversation partner of the user (for example, user A) of which the brain waves which are the biological information are measured corresponds to an example of the external stimulus, and the voice data indicating the voice corresponds to an example of the specific environment information.

In a case where the user A of which the brain waves are measured and the conversation partner are having a conversation, the processor 30 receives the brain waves measured from the user A who hears the voice of the conversation partner, and specifies the operation associated with the brain waves. For example, the processor 30 specifies the operation associated with the brain waves measured from the user A by referring to the management table shown in FIG. 4. The processor 30 may display an image indicating the content of the operation on the display unit of the UI 26, or may output a voice indicating the content of the operation from a speaker. In a case where an agreement to perform the operation is obtained from the user A, the processor 30 operates the device 22 by transmitting the control information for performing the operation to the device 22.

For example, the voice data indicating the voices of the user A and the conversation partner is measured by the microphone 14, and the processor 30 recognizes the content of the conversation between the user A and the conversation partner by analyzing the voice data measured by the microphone 14. The user A and the conversation partner may be imaged by the camera 16, and the processor 30 may recognize the user A and the conversation partner based on the imaged image data. The processor 30 recognizes the speech content of the conversation partner regarding the operation of the device 22, hears the speech, receives the brain waves measured from the user A, and transmits the control information for controlling the operation corresponding to the brain waves to the device 22. The speech content of the conversation partner regarding the operation of the device 22 corresponds to an example of the external stimulus, and the voice data indicating the speech content corresponds to an example of the specific environment information. The brain waves (for example, the brain waves measured for a time until a predetermined time elapses after a point of time at which the conversation partner speaks) measured after the conversation partner speaks are estimated to be the brain waves emitted from the user A who hears the speech of the conversation partner, that is, the brain waves emitted from the user A who receives the external stimulus.

A specific example will be described. In a case where the conversation partner speaks "Do you want to see OO on television?", the speech content is measured by the microphone 14, and the processor 30 recognizes the speech content by analyzing the voice measured by the microphone 14. The speech content is a speech related to an operation of a television which is the device 22, and corresponds to an example of the external stimulus, and the voice data indicating the speech content corresponds to an example of the specific environment information. The processor 30 receives the brain waves measured from the user A in response to the speech. For example, brain waves measured for a time until a predetermined time elapses after a point of time at which the conversation partner speaks "Do you want to watch OO on television?" are estimated to be the brain waves emitted from user A who hears the speech of the conversation partner. In a case where the brain waves are brain waves indicating consent, the processor 30 outputs a message of a content "Do you want to turn on television?". For example, the processor 30 may output the voice of the message from the speaker, or may display the message on the display unit of the UI 26. The processor 30 receives the brain waves measured from the user A after the message is output. In a case where the brain waves are brain waves indicating consent, the processor 30 turns on the power of the television by transmitting control information for performing an operation of turning on the television which is the device 22 to the television.

Modification Example 2

In Modification Example 2, the specific odor measured by the odor sensor 18 corresponds to an example of the external stimulus, and the odor data indicating the specific odor corresponds to an example of the specific environment information. For example, the odor around the user is measured by the odor sensor 18. The biological information is, for example, the brain waves. The specific odor is, for example, an odor related to the operation of the device 22. The biological information measured from the user after the odor data indicating the specific odor is measured is estimated to be biological information generated from the user who smells the specific odor which is the external stimulus. In this case, the processor 30 operates the device 22 based on the biological information generated from the user who smells the specific odor. That is, the processor 30 operates the device 22 based on the biological information generated from the user in response to the specific odor. For example, the biological information measured from the user for a time until a predetermined time elapses from at a point of time at which the specific odor is measured is estimated to be the biological information generated from the user who smells the specific odor which is the external stimulus.

In a case where the specific odor is measured, the processor 30 receives the brain waves measured from the user who smells the specific odor, and specifies the operation associated with the brain waves. For example, the processor 30 specifies the operation associated with the brain waves measured from the user by referring to the management table shown in FIG. 4. The processor 30 may display an image indicating the content of the operation on the display unit of the UI 26, or may output a voice indicating the content of the operation from the speaker. In a case where an agreement to perform the operation is obtained from the user, the processor 30 operates the device 22 by transmitting the control information for performing the operation to the device 22. The brain waves (for example, the brain waves measured for a time until a predetermined time elapses after a point of time at which the specific odor is measured) measured after the specific odor related to the operation of the device 22 is measured are estimated to be the brain waves emitted from the user who smells the specific odor, that is, the brain waves emitted from the user who receives the external stimulus.

A specific example will be described. After cooking, an odor during cooking remains in the room, and odor data indicating the odor is measured by the odor sensor 18. The odor is an odor related to an operation of an air cleaner which is the device 22, and corresponds to an example of the external stimulus, and the odor data indicating the odor corresponds to an example of the specific environment information. The processor 30 receives the brain waves measured from the user who smells the odor. For example, brain waves indicating "odor is uncomfortable" measured for a time until a predetermined time elapses after a point of time at which the odor after cooking is measured are estimated to be brain waves emitted from the user who smells the odor. In this case, the processor 30 outputs a message of the content "Do you want to turn on air cleaner?". For example, the processor 30 may output the voice of the message from the speaker, or may display the message on the display unit of the UI 26. The processor 30 receives the brain waves measured from the user after the message is output. In a case where the brain waves are brain waves indicating consent, the processor 30 turns on the power of the air cleaner by transmitting control information for performing an operation of turning on the air cleaner which is the device 22 to the air cleaner. An aroma diffuser for diffusing a scent may be used with the air cleaner or instead of the air cleaner.

Modification Example 3

In Modification Example 3, a temperature included in a specific temperature range measured by the temperature sensor 20 corresponds to an example of the external stimulus, and temperature data indicating the temperature included in the specific temperature range corresponds to an example of the specific environment information. For example, a temperature around the user is measured by the temperature sensor 20. The biological information is, for example, the brain waves. For example, the temperature included in the specific temperature range is a temperature related to the operation of the device 22. The biological information measured from the user after the temperature data indicating the temperature included in the specific temperature range is measured is estimated to be the biological information generated from the user who feels the temperature which is the external stimulus. In this case, the processor 30 operates the device 22 based on the biological information generated from the user who feels the temperature included in the specific temperature range. That is, the processor 30 operates the device 22 based on the biological information generated from the user who feels the temperature included in the specific temperature range. For example, the biological information measured from the user for a time until a predetermined time elapses after a point of time at which the temperature included in the specific temperature range is measured is estimated to be the biological information generated from the user who feels the temperature included in the specific temperature range which is the external stimulus.

When the temperature included in the specific temperature range is measured, the processor 30 receives the brain waves measured from the user who feels the temperature included in the specific temperature range, and specifies the operation associated with the brain waves. For example, the processor 30 specifies the operation associated with the brain waves measured from the user by referring to the management table shown in FIG. 4. The processor 30 may display an image indicating the content of the operation on the display unit of the UI 26, or may output a voice indicating the content of the operation from the speaker. In a case where an agreement to perform the operation is obtained from the user, the processor 30 operates the device 22 by transmitting the control information for performing the operation to the device 22. The brain waves (for example, the brain waves measured for a time until a predetermined time elapses after a point of time at which the temperature included in the specific temperature range is measured) measured after the temperature related to the operation of the device 22 is measured are estimated to be the brain waves emitted from the user who feels the temperature, that is, the brain waves emitted from the user who receives the external stimulus.

A specific example will be described. It is assumed that the room is hot at a time at which the user returns home, and a temperature equal to or greater than a predetermined threshold value is measured by the temperature sensor 20 installed in the room. The temperature equal to or greater than the predetermined threshold value is a temperature included in a specific temperature range, and is, for example, estimated to be a temperature at which a person generally feels hot. The temperature included in the specific temperature range is a temperature related to an operation of the air conditioner which is the device 22, and corresponds to an example of the external stimulus, and the temperature data indicating the temperature corresponds to an example of the specific environment information. The processor 30 receives the brain waves measured from the user who feels the temperature. For example, brain waves indicating "hot and uncomfortable" measured for a time until a predetermined time elapses after a point of time at which the temperature in the specific temperature range is measured are estimated to be the brain waves emitted from the user who feels the temperature. In this case, the processor 30 outputs a message of a content "Do you want to turn on air conditioner?". For example, the processor 30 may output the voice of the message from the speaker, or may display the message on the display unit of the UI 26. The processor 30 receives the brain waves measured from the user after the message is output. In a case where the brain waves are brain waves indicating consent, the processor 30 turns on the power of the air conditioner by transmitting control information for performing an operation of turning on the air conditioner which is the device 22 to the air conditioner.

Modification Example 4

In Modification Example 4, a specific situation viewed by the user of which the biological information is measured corresponds to an example of the external stimulus, and image data indicating the specific situation corresponds to an example of the specific environment information. For example, the user and the surroundings are imaged by the camera 16. The biological information is, for example, the brain waves. For example, the specific situation is a situation related to the operation of the device 22. The biological information measured from the user after the image data indicating the specific situation is measured is estimated to be biological information generated from the user who receives the specific situation which is the external stimulus. In this case, the processor 30 operates the device 22 based on the biological information generated from the user who receives the specific situation. That is, the processor 30 operates the device 22 based on the biological information generated from the user who views the specific situation. For example, the biological information measured from the user for a time until a predetermined time elapses after a point of time at which the image data indicating the specific situation is imaged is estimated to be the biological information generated from the user who views the specific situation which is the external stimulus.

For example, the processor 30 specifies a direction in which the user is viewing by analyzing the image data indicating the user and the surroundings, and recognizes the situation that the user is viewing.

In a case where the image data indicating the specific situation is imaged, the processor 30 receives the brain waves measured from the user who views the specific situation, and specifies an operation associated with the brain waves. For example, the processor 30 specifies the operation associated with the brain waves measured from the user by referring to the management table shown in FIG. 4. The processor 30 may display an image indicating the content of the operation on the display unit of the UI 26, or may output a voice indicating the content of the operation from the speaker. In a case where an agreement to perform the operation is obtained from the user, the processor 30 operates the device 22 by transmitting the control information for performing the operation to the device 22. The brain waves (for example, the brain waves measured for a time until a predetermined time elapses after a point of time at which the image data indicating the specific situation is imaged) measured after the image data indicating the specific situation related to the operation of the device 22 is imaged are estimated to be the brain waves emitted from the user who views the specific situation, that is, the brain waves emitted from the user who receives the external stimulus.

A specific example will be described. It is assumed that the user finds cotton dust falling on a floor, a scene in which the user is viewing this situation is imaged by the camera 16, and image data indicating this scene is generated. The situation in which the dust is falling on the floor is a situation related to an operation of a robot cleaner which is the device 22, and corresponds to an example of the external stimulus, and the image data indicating the situation corresponds to an example of the specific environment information. The processor 30 receives the brain waves measured from the user who views the situation. For example, brain waves indicating "dust is uncomfortable" measured for a time until a predetermined time elapses after a point of time at which the image data indicating a scene in which the user is viewing the dust falling on the floor is imaged are estimated to be the brain waves emitted from the user who views the situation. In this case, the processor 30 outputs a message of a content "Do you want to turn on robot cleaner?". For example, the processor 30 may output the voice of the message from the speaker, or may display the message on the display unit of the UI 26. The processor 30 receives the brain waves measured from the user after the message is output. In a case where the brain waves are brain waves indicating consent, the processor 30 turns on the power of the robot cleaner by transmitting control information for performing an operation of turning on the robot cleaner which is the device 22 to the robot cleaner.

In the exemplary embodiments above, the term "processor" refers to hardware in a broad sense. Examples of the processor includes general processors (e.g., CPU: Central Processing Unit), dedicated processors (e.g., GPU: Graphics Processing Unit, ASIC: Application Integrated Circuit, FPGA: Field Programmable Gate Array, and programmable logic device). In the exemplary embodiments above, the term "processor" is broad enough to encompass one processor or plural processors in collaboration which are located physically apart from each other but may work cooperatively. The order of operations of the processor is not limited to one described in the exemplary embodiments above, and may be changed.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing apparatus, comprising:
a processor; and
a memory coupled with the processor;
wherein manual operation information indicating that the following are associated:
a manual operation by a user for a device,
voice information indicating an operation of the device by a voice of the user, and
biological information other than the voice of the user at a time at which the voice is being uttering and are stored in the memory, and
wherein the processor is configured to operate the device with an operation specified by the manual operation information that associates between the voice information indicating the operation of the device by the voice of the user and the biological information other than the voice of the user at the time at which the voice is being uttering in a subsequent operation when:
(1) a difference between voice recognition information indicating the recognition result of the voice of the user at the time at which the user manually operates the device and the associated voice information is within a first allowable range, and (2) a difference between the biological information other than the voice of the user at the time at which the user manually operates the device and the associated biological information other than the voice is within a second allowable range.

2. The information processing apparatus according to claim 1,
wherein the manual operation information, voice information, and the biological information are associated for each user, and
the processor discriminates the voice for each user, and operates the device based on the biological information.

3. The information processing apparatus according to claim 1,
wherein the manual operation information, the voice information, and the biological information are associated for each user, and
the processor discriminates the voice for each user, and operates the device based on the biological information.

4. The information processing apparatus according to claim 1,
wherein the processor stops processing for associating voice information and the biological information with each other while the user is sleeping.

5. The information processing apparatus according to claim 1,
wherein the processor stops the operation using the biological information while the user is sleeping.

6. The information processing apparatus according to claim 1,
wherein the processor stops the operation using the biological information while the user is sleeping.

7. The information processing apparatus according to claim 1,
wherein the processor stops the operation using the biological information while the user is sleeping.

8. The information processing apparatus according to claim 2,
wherein the processor stops the operation using the biological information while the user is sleeping.

9. The information processing apparatus according to claim 3,
wherein the processor stops the operation using the biological information while the user is sleeping.

10. The information processing apparatus according to claim 1,
wherein, in a case where voices of a predetermined number of users or more are measured, the processor stops the operation using the biological information.

11. The information processing apparatus according to claim 1,
wherein the processor operates the device based on the biological information generated from the user who receives an external stimulus.

12. The information processing apparatus according to claim 11,
wherein the external stimulus is a voice of a conversation partner of the user.

13. The information processing apparatus according to claim 11, wherein the external stimulus is an odor.

14. The information processing apparatus according to claim 11, wherein the external stimulus is a temperature.

15. The information processing apparatus according to claim 11, wherein the external stimulus is a situation that the user views.

16. The information processing apparatus according to claim 1, wherein the biological information is brain waves.

17. A non-transitory computer readable medium storing a program causing a computer to execute:
storing manual operation information associating between:
a manual operation by a user for a device,
voice information indicating an operation of the device by a voice of the user, and
biological information other than the voice of the user at a time at which the voice is being uttering and are stored in the memory, and
operating the device with an operation specified by manual operation information that is associated with the voice information indicating the operation of the device by a voice of the user and the biological information other than the voice of the user at the time at which the voice is being uttering in a subsequent operation when:
(1) a difference between voice recognition information indicating the recognition result of the voice of the user at the time at which the user manually operates the device and the associated voice information is within a first allowable range, and (2) a difference between the biological information other than the voice of the user at the time at which the user manually operates the device and the associated biological information other than the voice of the user at the time at which the voice is being uttering is within a second allowable range.

18. A method, comprising:
storing manual operation information associating between:
a manual operation by a user for a device,
voice information indicating an operation of the device by a voice of the user, and biological information other than the voice of the user at a time at which the voice is being uttering; and operating the device with an operation specified by manual operation information that is associated with the voice information indicating the operation of the device by a voice of the user and the biological information other than the voice of the user at the time at which the voice is being uttering in a subsequent operation when:

(1) a difference between voice recognition information indicating the recognition result of the voice of the user at the time at which the user manually operates the device and the associated voice information is within a first allowable range, and (2) a difference between the biological information other than the voice of the user at the time at which the user manually operates the device and the associated biological information other than the voice of the user at the time at which the voice is being uttering is within a second allowable range.

* * * * *